United States Patent
Li et al.

(10) Patent No.: US 9,518,998 B2
(45) Date of Patent: Dec. 13, 2016

(54) DRUG TARGET CAPTURING METHOD

(71) Applicant: HitGen LTD., Chengdu (CN)

(72) Inventors: Jin Li, Chengdu (CN); Benyanzi Yang, Chengdu (CN); Dengfeng Dou, Chengdu (CN); Xiaohu Ge, Chengdu (CN); Hongmei Song, Chengdu (CN); Jinqiao Wan, Chengdu (CN); Yan Zhang, Chengdu (CN); Xiao Hu, Chengdu (CN); Xing Wang, Chengdu (CN); Jingchao Feng, Chengdu (CN); Guoqing Zhong, Chengdu (CN)

(73) Assignee: HitGen LTD., Changdu (CN)

( * ) Notice: Subject to any disclaimer, the term of this patent is extended or adjusted under 35 U.S.C. 154(b) by 0 days.

(21) Appl. No.: 14/945,438

(22) Filed: Nov. 19, 2015

(65) Prior Publication Data

US 2016/0154013 A1 Jun. 2, 2016

Related U.S. Application Data

(63) Continuation-in-part of application No. PCT/CN2014/077973, filed on May 21, 2014.

(30) Foreign Application Priority Data

May 21, 2013 (CN) .......................... 2013 1 0189932

(51) Int. Cl.
| | |
|---|---|
| *C12Q 1/68* | (2006.01) |
| *G01N 33/53* | (2006.01) |
| *G01N 33/94* | (2006.01) |
| *C12N 15/09* | (2006.01) |
| *G01N 33/58* | (2006.01) |

(52) U.S. Cl.
CPC .............. *G01N 33/94* (2013.01); *C12N 15/09* (2013.01); *G01N 33/582* (2013.01)

(58) Field of Classification Search
None
See application file for complete search history.

(56) References Cited

FOREIGN PATENT DOCUMENTS

WO WO-2011131693 A2 * 10/2011

* cited by examiner

*Primary Examiner* — James Martinell
(74) *Attorney, Agent, or Firm* — Wayne & King LLC

(57) ABSTRACT

The present invention discloses a method for capturing drug targets, comprising the following steps of: (1) preparing row materials, i.e., compounds and DNA or RNA or one party of other specific affinity materials; (2) linking: covalently linking the compounds to the DNA or RNA or the one party of other specific affinity materials, to obtain labeled compounds; (3) transferring: transferring the labeled compounds obtained in the step (2) into cells by a specific gene transfer method; (4) capturing targets: disrupting the cells in the step (3), and then capturing the DNA or RNA in the step (1) by immobilized complementary DNA or RNA, or capturing the one party of affinity materials in the step (1) by the other party of immobilized specific affinity materials, thus to enrich the targets through the covalently linked labeled compounds and the affinity of the targets; (5) identifying targets: dissociating the enriched targets from a stationary phase, deploying the targets by a gel electrophoresis method or by an equivalent separation method, and comparing differential proteins by proteomics thus to identify the potential targets; and (6) determining targets: expressing or purchasing the targets identified in the step (5) by priority, and comparing by interaction of the compounds with those targets one by one to determine the targets for the compounds. By the method of the present invention, compounds with low membrane permeability may be transferred into cells to be bound with the targets in the cells, to realize the target identification closer to the real physiological environment and thus provide more conclusive evidences for the acting mechanism of the compounds to diseases. Additionally, the method for capturing drug targets of the present invention is novel, easy, efficient, and low in cost, and has good application prospects.

7 Claims, 11 Drawing Sheets

| Target fishing | Negative control | Potential targets |
|---|---|---|
| Very long-chain specific acyl-CoA dehydrogenase, mitochondrial | Very long-chain specific acyl-CoA dehydrogenase, mitochondrial | |
| Keratin, type II cytoskeletal 1 | Keratin, type II cytoskeletal 1 | |
| Keratin, type II cytoskeletal 4 | Keratin, type II cytoskeletal 4 | |
| Keratin, type II cytoskeletal 2 epidermal | Keratin, type II cytoskeletal 2 epidermal | |
| Keratin, type II cytoskeletal 5 | Keratin, type II cytoskeletal 5 | |
| Keratin, type II cytoskeletal 6A | Keratin, type II cytoskeletal 6A | |
| Keratin, type I cytoskeletal 9 | Keratin, type I cytoskeletal 9 | |
| Keratin, type I cytoskeletal 10 | Keratin, type I cytoskeletal 10 | |
| Keratin, type I cytoskeletal 14 | Keratin, type I cytoskeletal 14 | |
| C-1-tetrahydrofolate synthase, cytoplasmic | C-1-tetrahydrofolate synthase, cytoplasmic | |
| Myosin-9 | Myosin-9 | |
| Acyl-CoA dehydrogenase family member 9, mitochondrial | | Acyl-CoA dehydrogenase family member 9, mitochondrial |
| Serum albumin | Serum albumin | |
| Hornerin | | Hornerin |
| Tubulin beta-4B chain | Tubulin alpha-1C chain | |
| Glutathione S-transferase Mu 2 | | Glutathione S-transferase Mu 2 |
| Tyrosine-protein phosphatase non-receptor type 1 | | Tyrosine-protein phosphatase non-receptor type 1 |
| 1-acyl-sn-glycerol-3-phosphate acyltransferase alpha | | 1-acyl-sn-glycerol-3-phosphate acyltransferase alpha |
| Serine/threonine-protein phosphatase PGAM5, mitochondrial | | Serine/threonine-protein phosphatase PGAM5, mitochondrial |
| Dermcidin | | Dermcidin |
| Lamin-B1 | | Lamin-B1 |
| Junction plakoglobin | | Junction plakoglobin |
| Tubulin alpha-1C chain | | Tubulin alpha-1C chain |
| Beta-actin-like protein 2 | Beta-actin-like protein 2 | |
| Glyceraldehyde-3-phosphate dehydrogenase | | Glyceraldehyde-3-phosphate dehydrogenase |
| Cytosolic phospholipase A2 beta | | Cytosolic phospholipase A2 beta |
| Zinc finger CCHC domain-containing protein 4 | Zinc finger CCHC domain-containing protein 4 | |
| Heat shock cognate 71 kDa protein | Heat shock cognate 71 kDa protein | |
| Tubulin alpha-3E chain | Tubulin alpha-3E chain | |
| Protein EURL homolog | | Protein EURL homolog |

Fig. 8

DRUG TARGET CAPTURING METHOD

CROSS-REFERENCE TO RELATED APPLICATIONS

This application is a continuation-in-part of International Patent Application No. PCT/CN2014/077973 with an international filing date of May 21, 2014, designating the United States, now pending, and further claims priority benefits to Chinese Patent Application No. 201310189932.0 filed May 21, 2013. The contents of all of the aforementioned applications, including any intervening amendments thereto, are incorporated herein by reference.

SEQUENCE LISTING

This application contains, as a separate part of the disclosure, a Sequence Listing in computer-readable form (filename: wk15_081_ST25.txt; created: Nov. 5, 2015; 474 bytes—ASCII text file) which is incorporated by reference in its entirety.

TECHNICAL FIELD

The present invention relates to a method for capturing drug targets.

BACKGROUND OF THE PRESENT INVENTION

The primary task of development of new drugs is to select and determine novel and effective drug targets. The determination of the drug targets is conducive to better understanding the function and acting mechanism of drugs in human bodies, and plays a vital role in oriented synthesis of drugs, efficacy, drug-delivery way, drug metabolism and safety evaluation. Substantially, there may be two ways in the prior art to capture drug targets. One way is to make a determination according to change in phenotype or function of cells, for example, biochips and capture technology based on yeast two-hybrid or three-hybrid; however, cells have complicated signaling pathways therein, a different signaling molecule may adjust a same cell function, and a same signaling molecule may play different roles in different signaling pathways, consequently, drug targets in cells can not be determined clearly according to the change in phenotype or function of cells. The other capture way is to capture potential drug targets with known drugs in cell lysis buffer according to the affinity between drugs and drug targets, however, different proteins in cells exist in different organelles which are independent small chambers separated from each other, and during lysis of cells, all proteins in the cells are mixed together; in this way, after addition of drugs, drugs may act on target proteins, on which drugs will not act in the normal physiological state, during whole-cell lysis, and this results in false positive results, interfering the capturing of drug targets. Most of drugs need to penetrate through the cell membrane to enter histocytes to play their due roles. However, the cell membrane, as a natural barrier, disables many molecules showing excellent in-vitro bioactivity (such as molecules having high polarity), including drugs, to enter the cells, so that the molecules can not play their due functions. As a result, the application of drugs is restricted.

In order to solve the problems of the existing methods in capturing drug targets, a new method for capturing drug targets is proposed, i.e., compounds are covalently linked to DNA or RNA or one party of other specific affinity materials, and then transferred into cells in such a way that no damage will be caused to the cells, for purpose of capturing drug targets in the cells; and finally the captured targets are identified and verified. An advantage of this new method is that the targets are captured in the cells. That is, compared with traditional methods in which the cell lysis is followed by capturing of targets, in the present invention, a process of binding compounds with targets occurs in cells, closer to the real physiological state. In this way, proteins in the cells may maintain their original conformations when binding occurs, so that it is able to better simulate the acting process of drugs in human bodies.

SUMMARY OF THE PRESENT INVENTION

In order to overcome defects in the prior art, the present invention provides a method for capturing drug targets.

The method for capturing drug targets of the present invention comprises the following steps of:

(1) Preparing row materials, i.e., compounds and DNA or RNA or one party of other specific affinity materials;

(2) Covalently linking the compounds to the DNA or RNA or the one party of other specific affinity materials, to obtain labeled compounds as shown in FIG. 1;

(3) Transferring: transferring the labeled compounds obtained in the step (2) into cells by a specific gene transfer method;

(4) Capturing targets: disrupting the cells in the step (3), and then capturing the DNA or RNA in the step (1) by immobilized complementary DNA or RNA, or capturing the one party of affinity materials in the step (1) by the other party of immobilized specific affinity materials, thus to enrich the targets through the covalently linked labeled compounds and the affinity of the targets;

(5) Identifying targets: dissociating the enriched targets from a stationary phase, deploying the targets by a gel electrophoresis method or by an equivalent separation method, and comparing differential proteins by proteomics thus to identify the potential targets; and (6) Determining targets.

The compounds in the step (1) are drugs themselves or ingredients of the drugs.

The labeled compounds in the step (2) refer to compounds linked to DNA or RNA tagged with biotin or fluorescein or isotope or other tags for tracing.

The target identification described in the step (5) is to dissociate the enriched targets from a stationary phase, deploy the enriched targets by a gel electrophoresis method, and compare differential proteins by proteomics thus to identify the potential targets.

The target determination described in the step (6) is to express or purchase the targets identified in the step (5) by priority, and compare by interaction of the compounds with those targets one by one to determine the targets for the compounds.

In the step (1), the molecular weight of the compounds ranges from 100 Da to 4000 Da.

In the step (1), the compounds are those which are used for the covalent linkage in the step (2), modified chemically and have bioactivity similar to that of the target compounds.

The DNA or RNA in the step (1) is any sequence within the range and has a functional group for the covalent linkage to the compounds in the step (2).

In the step (1), the length of the DNA or RNA is not less than five base pairs or bases.

In the step (1), the tag refers to biotin or fluorescein or isotope or other tags for tracing.

The one party of other affinity materials in the step (1) is one party of any pair of specific affinity materials having no obvious cytotoxicity and having covalent linkage to the compounds in the step (2).

The labeled compounds in the step (2) are those having bioactivity similar to that of the target compounds to be identified. In the step (3), the gene transfer method refers to all transfer methods by which no obvious damage will be caused to cells.

In the step (3), the gene transfer method refers to a cationic liposome transfection method, a calcium phosphate transfection method, a nanoparticles transfection method or an electroporation transfection method and other technical methods capable of transferring nucleic acid into cells.

The "gene transfer" refers to a process of transferring nucleic acid into cells physically, chemically or biologically.

The "specific affinity materials" refer to a pair of molecules capable of acting on and specifically bonding with each other, for example, complementary nucleic acid fragments, enzyme and substrate, enzyme and inhibitor, enzyme and coenzyme, hormone and cell receptor, vitamin and binding protein, and antibody and antigen.

In the step (1), when the NDA or RNA is in a random double-stranded sequence, the complementary DNA or RNA for capturing in the step (4) is a single-stranded sequence capable of being complementary with one strand of the random double-stranded sequence. During capture, it is necessary to unwind the random double-stranded sequence first.

In the step (6), the interaction refers to the affinity between targets and unmodified compounds.

In the step (6), the priority refers to sorting potential target proteins by priority according to the (relative) abundance after removing cytoskeleton proteins from the differential proteins.

By the method of the present invention, compounds with low membrane permeability may be transferred into cells to be bound with the targets in the cells, to realize the target identification closer to the real physiological environment and thus provide more conclusive evidences for the acting mechanism of the compounds to diseases. Additionally, the method for capturing drug targets of the present invention is novel, easy, efficient, and low in cost, and has good application prospects.

Apparently, according to the content of the present invention, various modifications, replacements and alterations in other forms may be made in accordance with common technical knowledge and conventional methods of the art, without departing from the basic technical concept of the present invention.

The content of the present invention will be further described in detail by specific implementations in the form of embodiments. However, it should not be interpreted as limiting the scope of the subject of the present invention only to the following embodiments. Techniques realized based on the content of the present invention shall all fall into the scope of the present invention.

BRIEF DESCRIPTION OF THE DRAWINGS

FIG. 8 shows comparison of differential proteins and identification of potential targets.

DETAILED DESCRIPTION OF THE PRESENT INVENTION

Embodiment 1

Figure 1:
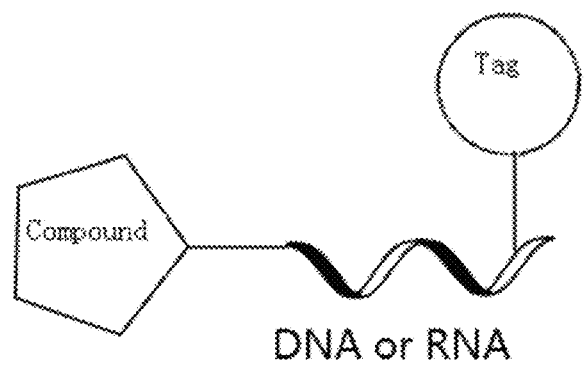
FIG. 1 shows a general structural formula of molecules of labeled compounds.

1. Synthesis of Labeled Compounds 1.1 Selection of linking sites of compounds: a reaction site, having no influence on the activity of the compounds, was determined according to the structure-function relationship of the compounds;

1.2 Modification of compounds: the compounds were modified by a bifunctional reagent, wherein the unreacted functional group should be compatible with reactions for the labeled compounds;

1.3 Modification of DNA or RNA or one party of other specific affinity materials: the modification was performed by a bifunctional reagent; and 1.4 Synthesis of labeled compounds: the modified compounds were covalently bonded to the modified DNA or RNA or one party of other specific affinity materials.

2. Transfer of Labeled Compounds into Cells

The labeled compounds were transferred into cells by a gene transfer method, which was suitable for transferring compounds and by which no obvious damage will be caused to cells, including a cationic liposome transfection method, a calcium phosphate transfection method, a nanopartides transfection method or an electroporation transfection method and other technical methods capable of transferring nucleic acid into cells.

3. Capture of Targets 3.1 A RIPA lysis buffer was dissolved at room temperature, added with a protease inhibitor and placed on ice for later use.

3.2 The mixture was washed with PBS once, and cells were scraped off by a cell scraper. The mixture was centrifuged and the cells were collected, with cell sediments left for later use.

3.3 200 μL of cell lysis buffer with the protease inhibitor added therein was added per 20 μL of cell sediments.

3.4 Reaction in ice bath lasted for 30 min.

3.5 14000 g of the mixture was centrifuged for 10 min at 4T.

3.6 The supernatant was extracted immediately to a pro-cooled plastic tube, i.e., the extracted cytoplasmic protein. The extracted cytoplasmic protein may be used immediately or frozen at −70° C.

3.7 Magnetic beads or other immobilized high-affinity materials, containing a binding buffer having a volume twice as much as that of the lysis buffer, were added according to the volume of the lysis buffer, and was incubated for 20 min.

3.8 The magnetic beads were adsorbed by a magnet or other immobilized high-affinity materials were filtered, and were cleaned with 20 mM Tris-HCl (pH 8.0) for three times.

3.9 A small amount of 20 mM Tris-HCl buffer was added and heated for 3 min at 80° C.; then, the supernatant was extracted quickly; and the sample was silver stained after being further deployed with SDS-PAGE.

4. Target Identification 4.1 Protein bands and the blank control were subject to protein identification by mass spectrometry, to obtain detailed information about proteins bound to compounds.

4.2 The proteins enriched based on the affinity were compared with the blank control to determine potential compound targets.

5. Target Determination 5.1 The potential compound targets identified in 4.2 were expressed or purchased by priority.

5.2 The potential targets were subject to affinity experiments by the compounds one by one, and compared to finally determine the targets for the compounds.

Beneficial effects of the present invention are verified by the following embodiments:

Embodiment 1

Synthesis of the Labeled Compound 1

1. Experimental Materials and Reagents

The compound 1-1 was synthesized by our company according to the method as described in the reference document (D. P. Wilson et al, J. Med. Chem. 2007, 50, 4681-4698); polyA (5'-(CH2)12-A19-3'-FITC) modified by 5'-amino and 3'-fluorescein was purchased from Invitrogen Trading Shanghai Co., Ltd; and the other reagents used for chemical synthesis were purchased from Aldrich or TCI.

2. Synthesis of the Labeled Compound 1

Synthesis Route of the Labeled Compound 1:

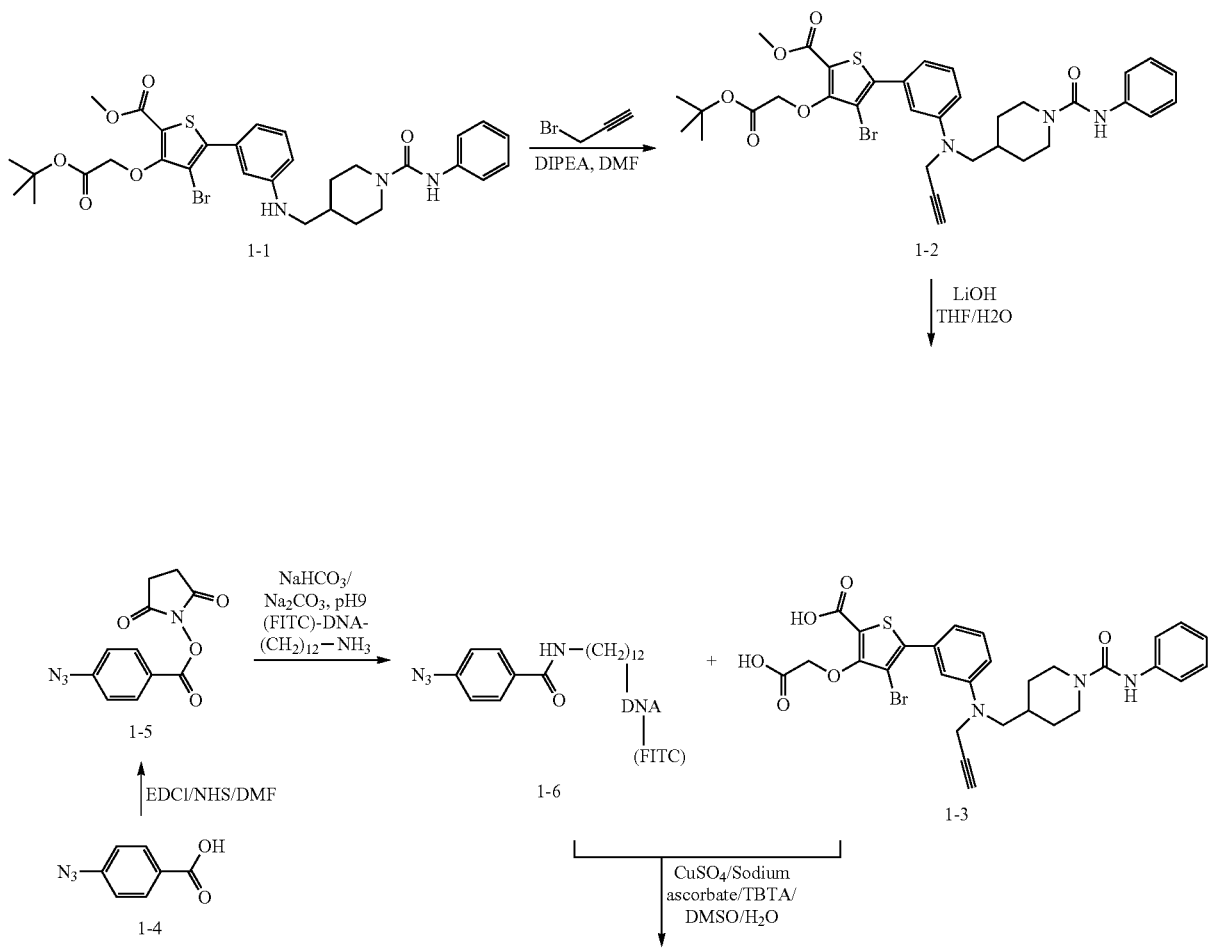

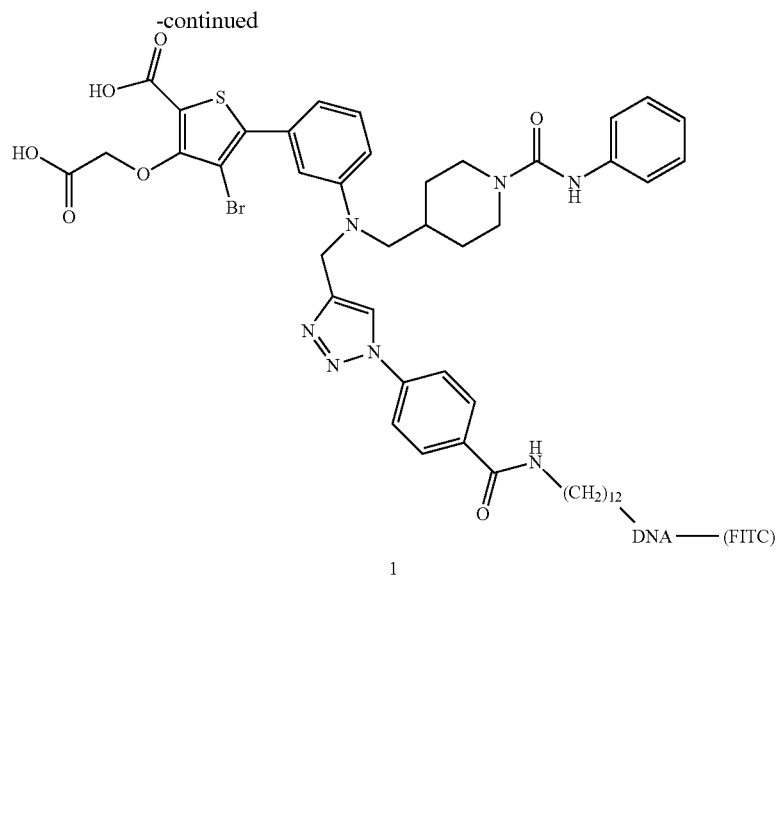

Compound 1-2: 4-bromo-3-oxo-tert-butyl acetate-5-(3-(((1-phenyl carbamoylpiperidine)-4-methyl)-N-propargyl amine)phenyl)thiophene-2-methyl formate 4-bromo-3-oxo-tert-Butyl acetate-5-(3-(((1-phenyl carbamoylpiperidine)-4-methy)-phenyl)thiophene-2-methyl formate (1-1) (250 mg, 0.4 mmol), propargyl bromide (70 mg, 0.5 mmol) and N,N-diisopropylethylamine (1.5 mL) were dissolved into 20 mL of N,N-dimethylformamide, stirred for 5 h at 90° C., cooled to room temperature and distilled under reduced pressure to obtain a crude product; and the crude product was separated by column chromatography to obtain 4-bromo-3-oxo-tert-butyl acetate-5-(3-(((1-phenyl carbamoylpiperidine)-4-methyl)-N-propargyl amine)phenyl)thiophene-2-methyl formate (2) (white solid, 130 mg, with a yield of 49%). MS m/z (ESI): 668,670 (M+H)$^+$; 690, 692 (M+Na)$^+$.

Figure 2:
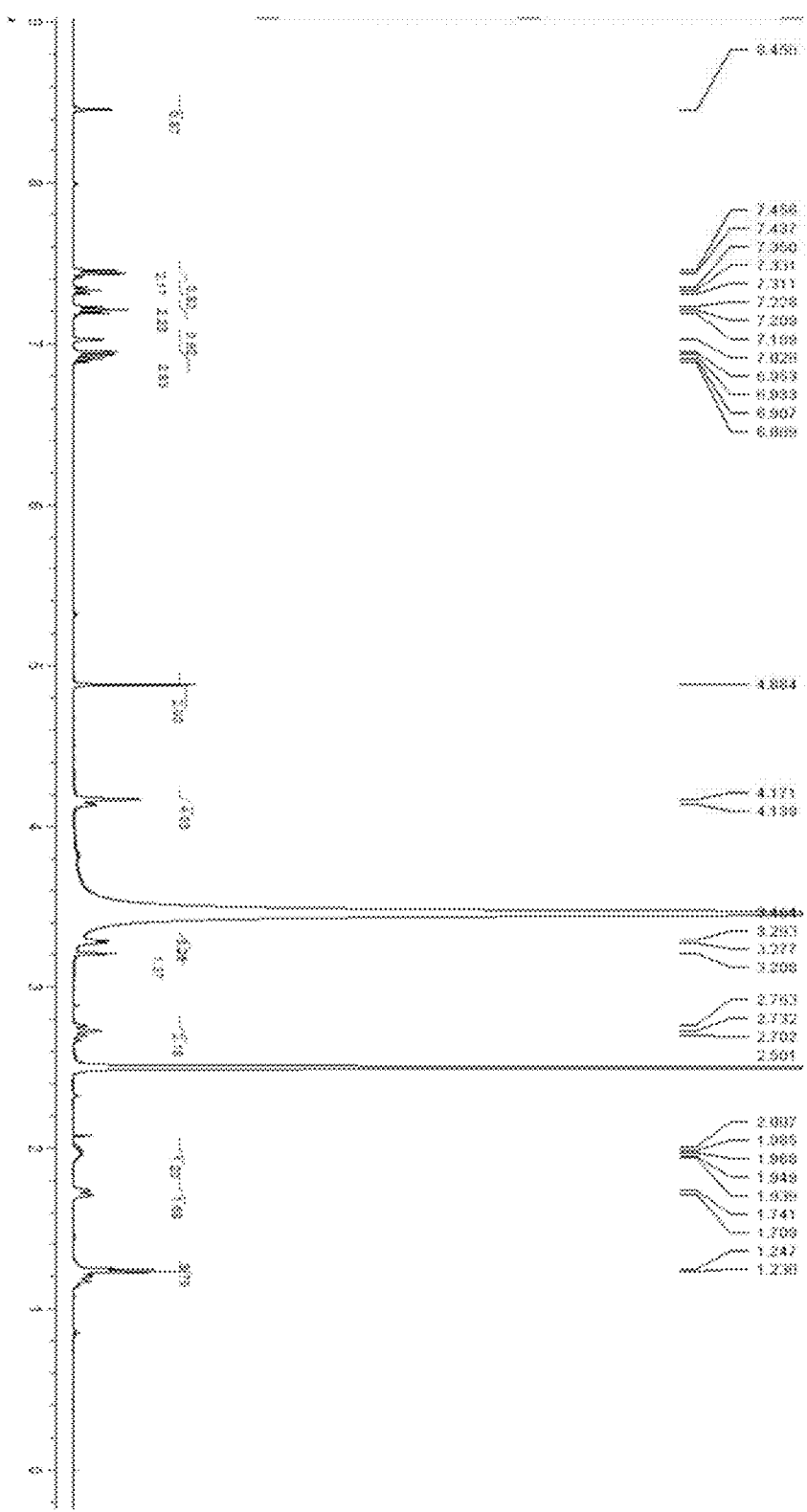
FIG. 2 is a $^1$H NMR curve of a compound 1-3.

Compound 1-3: 4-bromo-3-oxoacetic acid-6-(3-(((1-phenyl carbamoylpiperidine)-4-methyl)-N-propargyl amine)phenyl)thiophene-2-formic acid Lithium hydroxide (200 mg, 2.38 mmol) was added to 4-bromo-3-oxo-tert-butyl acetate-5-(3-(((1-phenyl carbamoylpiperidine)-4-methyl)-N-propargyl amine)phenyl)thiophene-2-methyl formate (1-2) (100 mg, 0.15 mmol) in 5 mL of tetrahydrofuran and 5 mL of aqueous solution, and stirred overnight at room temperature. 2N hydrochloric acid was added to the reaction solution; and the reaction solution was acidified until the pH became 2, and then concentrated to obtain a crude product. The crude product was treated by HPLC to obtain 4-bromo-3-oxoacetic acid-5-(3-(((1-phenyl carbamoylpiperidine)-4-methyl)-N-propargyl amine)phenyl)thiophene-2-formic acid (1-3) (white solid, 40 mg, with a yield of 42%). MS m/z (ESI): 626,628 (M+H)$^+$; $^1$H NMR (CDCl3): δ8.45 (s, 1H), 7.43 (m, 2H), 7.33 (t, J=7.6 Hz, 1H), 7.21 (m, 2H), 7.03 (s, 1H), 6.92 (m, 3H), 4.88 (s, 2H), 4.15 (m, 4H), 3.28 (m, 2H), 3.20 (m, 1H), 2.70 (m, 2H), 1.82 (m, 1H), 1.73 (m, 2H), 1.24 (m, 3H). (See FIG. 2 for $^1$H NMR)

Compound 1-5: 4-azidobenzoate succinimide ester

Figure 3:
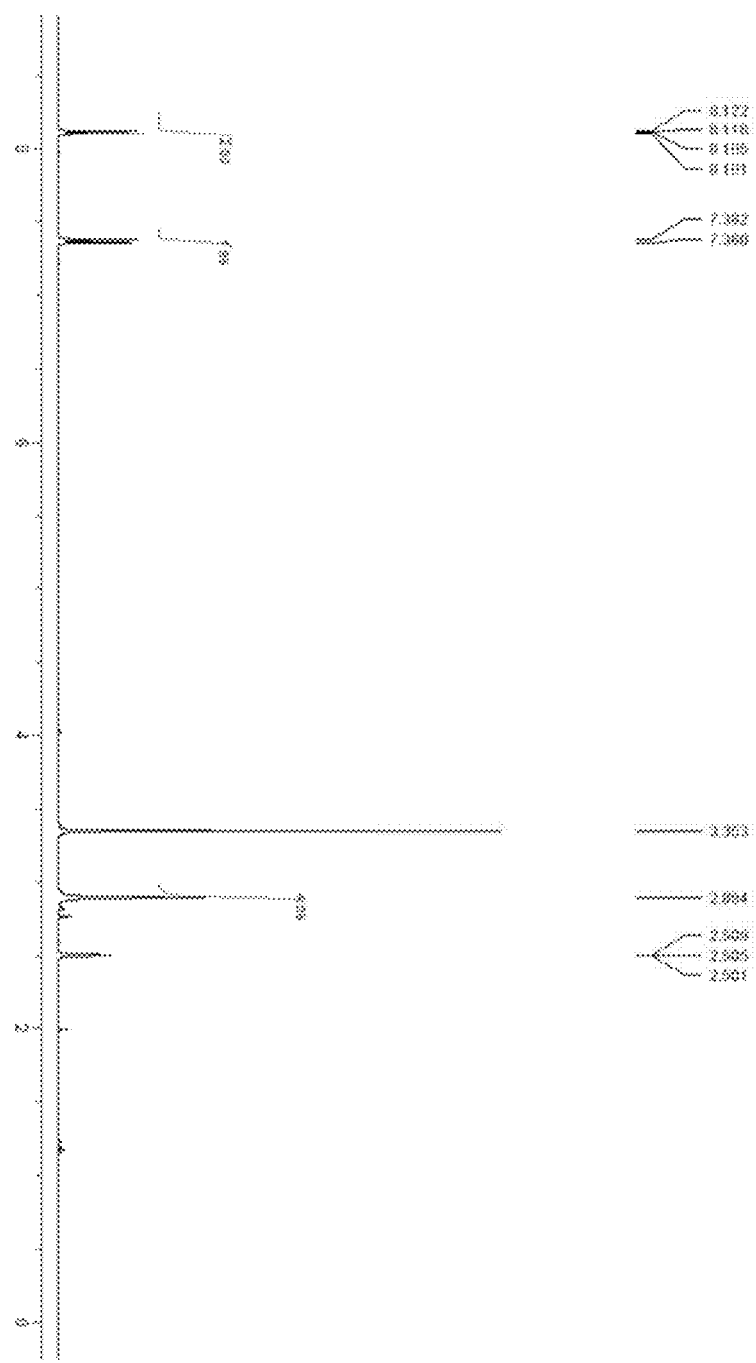
FIG. 3 is a $^1$H NMR curve of a compound 1-5.

In ice bath, 1-ethyl-3-(3-dimethylamine propyl) carbodiimide hydrochloride (EDCI, 570 mg, 3.7 mmol) was added to 10 mL of N,N-dimethylformamide containing 4-azidobenzoic acid (500 mg, 3.06 mmol), and then N-hydroxysuccinimide (440 mg, 3.7 mmol) was added thereto. The reaction lasted for 1 h away from light and under protection of nitrogen; and then, the reaction solution was heated to the room temperature, and stirred overnight away from light. N,N-dimethylformamide was removed by distillation under reduced pressure; and then, the residues were dissolved in ethyl acetate and washed with water for three times; and finally, the organic phase was dried by anhydrous sodium sulfate, filtered and concentrated to obtain a crude product. The crude product was separated by column chromatography to obtain the product 4-azidobenzoate succinimide ester (1-5) (white solid, 780 mg, with a yield of 97.5%). $^1$H NMR (DMSO-de): δ8.11 (d, J=8.4 Hz, 2H), 7.37 (d, J=8.4 Hz, 2H), 7.37 (s, 4H). (See FIG. 3 for $^1$H NMR)

Compound 1-6: 4-azidobenzamide 12-alkyl 19 polyA fluorescein

A mixture of polyA (5'-(CH$_2$)$_{12}$-A$_{19}$-3'-FITC) (50 nmol) modified by 5'-amino and 3'-fluorescein, the 4-azidobenzoate succinimide ester (1-5) (5 μmol, 100 eq.) in 500 μL of 0.5 M sodium carbonate/sodium bicarbonate buffer (pH 9), and 500 μL of dimethylsulfoxide was shaken overnight in a low speed at room temperature. Then, the reaction system was directly separated by reverse HPLC column chromatography, and lyophilized to obtain 4-azidobenzamide 12-alkyl 19 polyA fluorescein (1-6) (light yellow solid, with a yield of over 90%).

Figure 4:
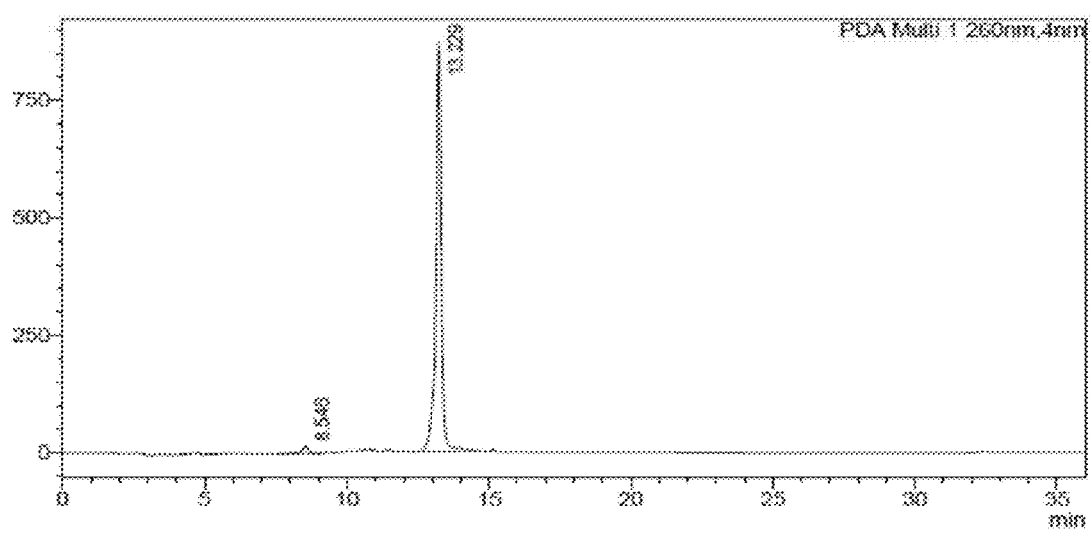
FIG. 4 is HPLC purity analysis of a labeled compound 1.
Figure 5:
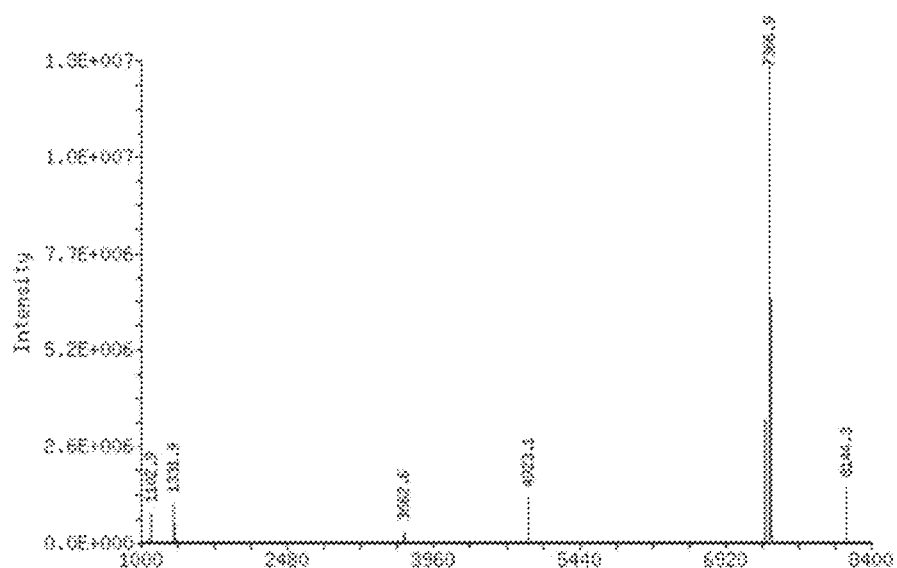
FIG. 5 is mass-spectrometric analysis of the labeled compound 1.

The labeled compound 1: 4-bromo-3-oxoacetic acid-5-(3-(((1-(4-fluorescein 19 polyadenosinic acid) 12-alkyl acetamidophenyl)-1H-1,2,3-triazole-4-methylene)(1-Phenyl ammonia formylpiperidine)-4-methyl)amino)phenyl)thiophene-2-formic acid 30 μL of solution A (copper sulfate and tris[(1-benzyl-1H-1,2,3-triazol-4-yl)methyl]amine were dissolved at a mole ratio of 1:2 into a solution composed of water, dimethylsulfoxide and tert-butanol at a volume ratio of 4:3:1, with a concentration of 10 mM) was added to solution B (4-azidobenzamide 12-alkyl 19 polyA fluorescein (1-6) (15 nmol) in 200 μL of aqueous solution and 4-bromo-3-oxoacetic acid-5-(3-(((1-phenyl carbamoylpiperidine)-4-methyl)-N-propargyl amine)phenyl)thiophene-2-formic acid (1-3) (960 nmol)) in 50 μL of DMSO solution, and vortex-centrifuged; and subsequently, 60 μL of newly-prepared sodium ascorbate (600 nmol) in aqueous solution was added to the reaction system, and then shaken overnight in a low speed at room temperature. Then, the reaction solution was directly separated by reverse HPLC column chromatography and purified to obtain the product 4-bromo-3-oxoacetic acid-5-(3-(((1-(4-fluorescein 19 polyA) 12-alkyl acetamidophenyl)-1H-1,2,3-triazole-4-methylene)((1-phenylcarbamoylpiperidine)-4-methyl)amino)phenyl)thiophene-2-formic acid (1) (light yellow solid, with a yield of 80%). (The HPLC purity analysis of the labeled compound 1 is as shown in FIG. 4, and the mass-spectrometric analysis of the labeled compound 1 is as shown in FIG. 5)

3. Synthesis of the Contrast Compound 2

Synthesis Route of the Contrast Compound 2:

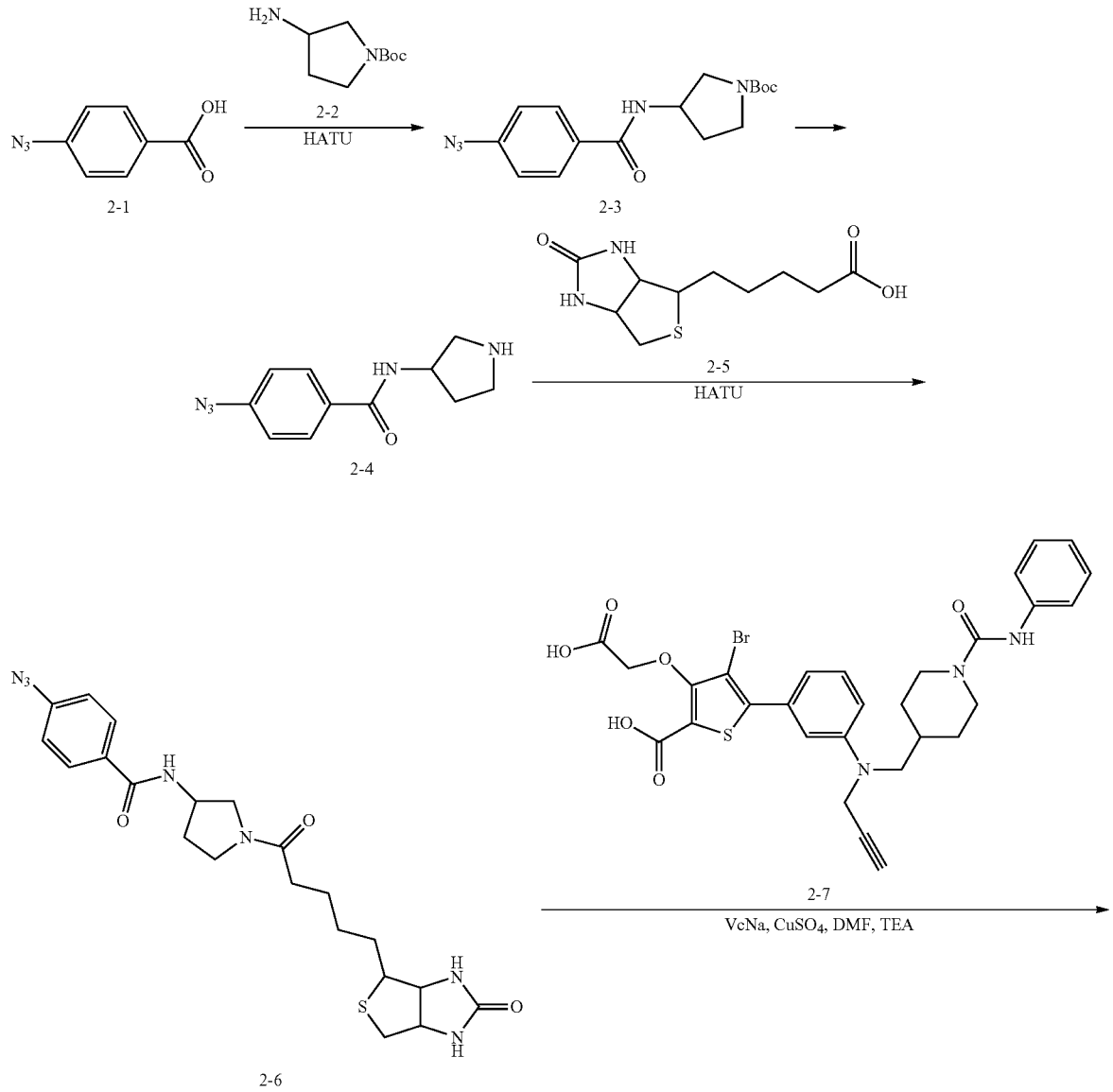

-continued

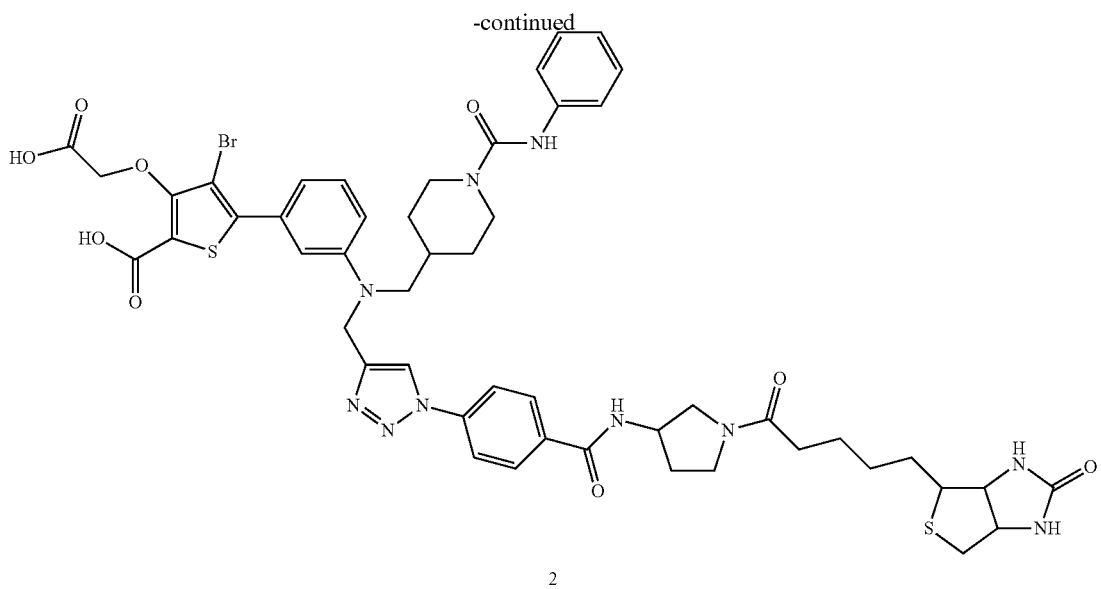

2

Compound 2-3: N-boc-3-(4-azidobenzamido)pyrrole

Azidobenzoic acid (2-1) (326 mg, 2 mmol), N-boc-3-aminopyrrole (2-2) (372 mg, 2 mmol), HATU (1.14 g, 3 mmol) and N,N-diisopropylethylamine (1.5 mL) were dissolved into 20 mL of dichloromethane, stirred for 2 h at room temperature, diluted with dimethylmethane, and then washed with water for three times and with saturated salt water for three times, successively; and the organic phase was dried by anhydrous sodium sulfate, filtered and concentrated to a crude product. The crude product was separated by column chromatography to obtain N-boc-3-(4-azidobenzamido)pyrrole (2-3) (yellow oily liquid, 503 mg, with a yield of 98%). MS m/z (ESI): 276 (M-tBu+H)$^+$332 (M+H)$^+$; 354 (M+Na)$^+$. 276 (M-tBu+H)$^+$ 332 (M+H); 354 (M+Na)$^+$.

Compound 2-4:
4-azido-N-(3-pyrrolidinyl)benzamide

Trifluoroacetic acid (1 ml) was added to N-boc-3-(4-azidobenzamido)pyrrole (2-3) (503 mg, 1.5 mmol) in 5 ml of dichloromethane solution, and stirred for 2 h at room temperature. The mixture was concentrated to obtain a crude product 4-azido-N-(3-pyrrolidinyl)benzamide (2-4) (yellow oily liquid, 340 mg, with a yield of 76%) MS m/z (ESI): 232 (M+H)$^+$.

Compound 2-6: 4-azido-N-(1-(5-(2-oxohexahydro-1H-thieno[3,4-d]imidazole-4-yl)pentanoly)pyrrolidine-3-yl)benzamide 4-azido-N-(3-pyrrolidinyl)benzamide (2-4) (340 mg, 1.5 mmol), biotin (2-5) (439 mg, 1.8 mmol), HATU (684 mg, 1.8 mmol) and N,N-diisopropylethylamine (1 mL) were dissolved into 20 mL of dichloromethane, stirred for 2 h at room temperature, diluted with dimethylmethane, and then washed with water for three times and with saturated salt water for three times, successively; and the organic phase was dried by anhydrous sodium sulfate, filtered and concentrated to a crude product. The crude product was separated by column chromatography to obtain (2-6) (yellow oily liquid, 458 mg, with a yield of 67%). MS m/z (ESI): 458 (M+H)$^+$.

Contrast Compound 2: 4-bromo-3-carboxymethoxy-5-(3-(((1-(4-((1-(5-(2-oxohexahydro-1H-thieno[3,4-d]imidazole-4-yl)valeryl)pyrrolidine-3-yl)carbamoyl)phenyl)-1H-1,2,3-triazol-4-yl)methyl)((1-(phenylcarbamoyl)piperidine-4-yl)methyl)amino)phenyl)thiophene-2-formic acid The compound (2-6) (23 mg, 50 umol), 4-bromo-3-oxoacetic acid-5-(3-(((1-phenyl carbamoylpiperidine)-4-methyl)-N-propargyl amine)phenyl)thiophene-2-formic acid (2-7) (31 mg, 50 umol), copper sulfate (2.5 mg, 10 umol), sodium ascorbate (4 mg, 20 umol), and triethylamine (7 ul, 50 umol) were dissolved into 5 mL of N,N-dimethylformamide and 0.5 mL of water, stirred for 2 h at room temperature, and distilled under reduced pressure to obtain a crude product. The crude product was treated by HPLC to obtain (2) (yellow solid, 30 mg, with a yield of 55%). MS m/z (ESI): 1085 (M+H)$^+$. $^1$H NMR (400 MHz, DMSO-d6): δ 8.82 (s, 1H), 8.69 (dd, J=6.4, 15.6 Hz, 1H), 8.46 (s, 1H), 8.01 (m, 4H), 7.45 (d, J=7.6 Hz, 2H t), 7.29 (t, J=8.0 Hz, 1H), 7.21 (d, J=7.6 Hz, 1H), 7.00 (m, 2H), 6.85 (d, J=8.0 Hz, 1H), 6.45 (s, 1H), 6.36 (s, 1H), 4.87 (s, 2H), 4.76 (s, 2H), 4.15-4.52 (m, 5H), 3.4-3.7 (m, 7H), 2.59-3.1 (m, 6H), 1.9-2.3 (m, 6H), 1.2-1.8 (m, 11H).

Embodiment 3

Transfer of the Labeled Compound 1

1. Experimental Materials and Reagents

The HepG2 cell strains were purchased from Shanghai Institutes for Bioscience Chinese Academy of Sciences; the RPMI-1640 culture medium was purchased from Hyclone Shanghai; the fetal bovine serum was purchased from Tianjin Hao Yang Biological Products Co., Ltd.; the trypsin and Opti-MEM were purchased from Invitrogen Shanghai; the X-tremeGENEsiRNA transfection reagent was purchased from Roche China; and the cell culture dishes and other consumables were all purchased from Corning China.

5'-$NH_2$—$(CH_2)_{12}$—$PO_4$-$A_5$-3'-FITC, 5'-$NH_2$—$(CH_2)_{12}$—$PO_4$-$A_{19}$-3'-FITC, 5'-CAGCAGTTTGGCCA-GCCCA-3' (SEQ ID NO:1) and 5'-$NH_2$—$(CH_2)_{12}$—$PO_4$-TGGGCTGGCCAAACTGCTG-3'-FITC (SEQ ID NO:2) were all synthesized by Invitrogen Trading Shanghai Co., Ltd.

2. Cell Preparation Before Transfer of Small-Molecule Compounds 24 h before transfer, the HepG2 cells in the phase of logarithmic growth were digested with trypsin; a culture medium containing 10% serum was used for adjusting the cell density to $0.5 \times 10^6$ cells/mL; and the cells were inoculated again in a cell culture dish of 15 cm and cultured in a culture incubator containing 5% $CO_2$ at 37° C. The cells may be used for experiments when the cell density reaches 60% to 70% 24 h later.

3. Transfer of Small-Molecule Compounds 4 nmol of labeled compound 1 was added to a sterile centrifuge tube (tube A) of 15 mL, and uniformly mixed with Opti-MEM in a corresponding volume, with a total volume of 2 mL; the tranfection reagent was shaken gently, and 160 μL of tranfection reagent was mixed with 1.84 mL of Opti-MEM in another tube (tube B); and the solution in the tube A was mixed with the solution in the tube B, the mixture was slightly triturated by a pipette and incubated for 20 min at room temperature.

Figure 6:
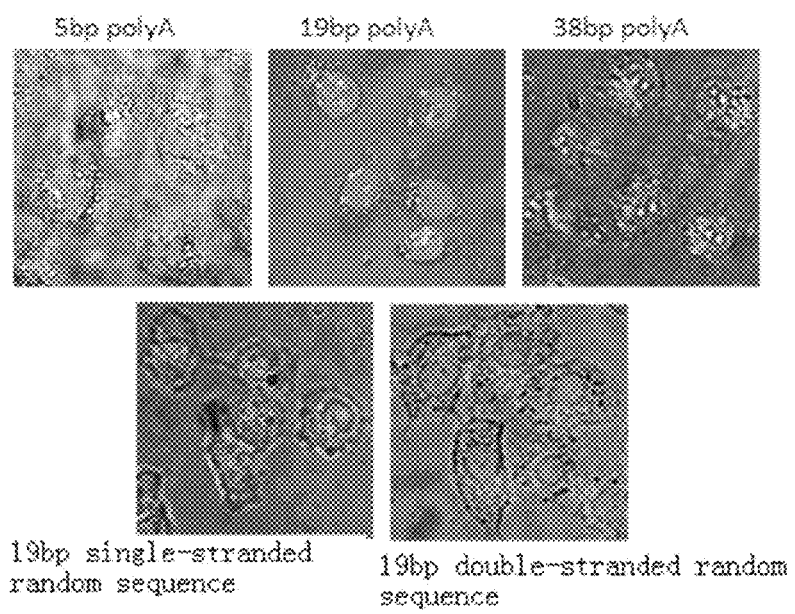
FIG. 6 shows positioning, by laser confocal microscopy, of the labeled compound 1 in cells (those in blue are cell nucleus, and those in green are FITC-tagged labeled compounds 1).

6 mL of RPMI-1640 serum-free culture medium was added to the mixture and mixed uniformly; the primary culture medium in the HepG2 cell culture dish was discarded, and slightly triturated with RPMI-1640 serum-free culture medium once; and then, the mixture was moved into the HepG2 cell culture dish, and cultured in a culture incubator containing 5% $CO_2$ at 37° C. 6 h later, the positioning, by laser confocal microscopy, of the compounds in the cells was as shown in FIG. 6. The single-stranded and double-stranded DNA or RNA random or polyA fragments of greater than 5 bp may be all transferred into cells by X-tremesiRNA, with most of them into the cytoplasm and a few of them into the cell nucleus.

4. Collection of Cracked Cells and Extraction of Total Proteins

A culture medium containing the mixture of the labeled compound 1 and transfection reagent was removed after being cultured for 6 h; 10 mL of PBS (pH 7.4) was added to the culture dish, shaken left and right gently to wash the residual mixture, and then removed; 6 mL of trypsin solution was added, and shaken gently so that the trypsin solution covers all cells; the culture dish was kept standing for 2 to 3 min at room temperature, and then slightly triturated with a sucker; and the cell suspension was transferred to a centrifuge tube of 15 mL to be centrifuged for 10 min at room temperature in a speed of 1000 rpm.

The supernatant was discarded, 1 mL of PBS was added to re-suspend cells, and the cell resuspension was centrifuged for 10 min at room temperature in a speed of 1000 rpm.

A total volume of 3 mL of cell laysis buffer and 30 μL of cocktail protease inhibitor were added, and treated in ice bath for 15 to 20 min until the cells were completely cracked.

Embodiment 4

Capture of Target Proteins from the Transferred Cell Lysates by Oligo(dT) Magnetic Beads Together with Labeled Compound 1

1. Materials and Reagents

Oligo-dT magnetic beads: Dyna Magnetic Bead®Oligo $(dT)_{25}$ (Life Technologies)

Binding buffer: 20 mMTris-HCl, 50 mM LiCl, 2 mM EDTA and PH 7.5.

Elution buffer: 10 mM Tris-HCl and PH 7.5.

Silver stain kit: Pierce Silver Stain Kit for Mass Spectrometry.

2. Capture of Targets 2.1 Activation of magnetic beads: 400 μL of magnetic beads was placed into a centrifuge tube of 1.5 mL. The magnetic beads were washed with a binding buffer in a same volume as the magnetic beads, so that the magnetic beads were suspended in the binding buffer. This mixture is defined as "magnetic bead suspension", for later use.

2.2 Binding: 4.5 mL of magnetic bead suspension was mixed with HepG2-PT lysates to which 3 mL of labeled compound 1 has been transferred, and incubated for 20 to 30 min at room temperature away from light.

2.3 Washing: the magnetic beads were adsorbed to the bottom of the tube by a magnet, and the supernatant 1 was collected. The elution buffer was added to re-suspend the magnetic beads, and the supernatant 2 was collected after the magnetic beads are adsorbed. The washing was repeated once, and the supernatant 3 was collected.

2.4 Release: 20 μL of elution buffer was added to an EP tube to re-suspend the magnetic beads, and the EP tube was placed on the magnet immediately after being heated for 3 min at 80° C. The supernatant was collected to obtain "released substance".

2.5 SDS-PAGE: 20 μL of released substance and the upper sample of blank cell lysis buffer were subject to electrophoresis. The proteins were detected by silver staining at end of the electrophoresis.

Embodiment 5

Capture of Target Proteins Directly from Cell Lysates by Biotin Together with Contrast Compound 2

1. Collection of Cracked Cells and Extraction of Total Proteins

RIPA protein lysis buffer was dissolved at room temperature, and placed on ice for later use. 10 mL of PBS (pH 7.4) was added, shaken left and right gently to wash the residual mixture, and then removed; 0.5 mL of protein lysis buffer was added, and shaken gently so that the protein lysis buffer covers all cells; the cells were scraped off by a cell scraper gently, and the cell suspension was transferred to a centrifuge tube of 2 mL; then, 0.5 mL of protein lysis buffer was added, cells were scraped off the plate by the cell scraper gently once, and the cell suspension was transferred to the same centrifuge tube, treated for 1 h in ice bath, and then treated ultrasonically until the cells are completely cracked (the conditions of ultrasonic treatment: total five cycles of operating for 2 s and stopping for 4 s). The lysis buffer was centrifuged for 10 min at 4° C. in a speed of 10000 rpm, and the supernatant was collected for experiments.

2. Co-Incubation of Contrast Compound 2

500 μL of supernatant was added to each of two centrifuge tubes of 5 mL, respectively marked as tube ① and tube ②, 2 nmol of contrast compound 2 was added to ① and no contrast compound 2 to ② as a negative control. The solution in ① and the solution in ② were uniformly mixed upside down, and then incubated for 1 h at 4° C.

3. Capture of Targets 3.1 Materials and Reagents
Binding buffer: 100 mM PBS, 150 mM NaCl, pH 7.2; elution buffer: SDS-Sample buffer; and a centrifugal column
3.2 Binding
The desired buffer and streptavidin medium were balanced to room temperature; then, the streptavidin medium was added to the centrifugal column, placed in a collection tube, and centrifuged for 1 min to remove the medium stock solution; the binding buffer in a same volume was added to the centrifugal column and centrifuged for 1 min; and the eluant was discarded. The above steps were repeated twice, and the eluant was discarded. The centrifugal column was placed in a new collection tube, added with a sample/control, slightly triturated and uniformly mixed, and subsequently incubated for 10 min at room temperature. The binding buffer with a same volume was added to the centrifugal column, and centrifuged for 1 min; and the eluant was discarded. The above steps were repeated for four times, and the eluant was discarded. The medium was sucked out after the last elution, and added with the elution buffer for treating for 10 min in boiling water bath to release proteins.

4. Silver staining 4.1 Reagents
Stationary liquid: 50% MeOH, 10% HAC and 40% $H_2O$.
Silver stain solution: 21 ml of 0.36% NaOH+1.4 mL of ammonia (the content of which is approximately 28% to 30%)+4 mL of (20% $AgNO_3$), as well as water added until the volume became 100 mL. The silver stain solution should be used in 15 min ($AgNO_3$ needed to be added slowly, and stirred all the time until the color was not yellow any longer)
Developing solution: 0.5 mL of 1% citric acid+50 μL of formaldehyde (the content of which is 37% to 40%), as well as water added until the volume became 100 mL.
Stop solution: 1% acetic acid
Protein Maker
SDS-PAGE Precast Gel
4.2 Silver Staining
The collected sample/control and protein Maker were subject to electrophoresis at 90 eV, added with the stationary liquid to immobilize for h, washed with deionized water for three times each for 10 min, silver stained for 15 min, washed with deionized water for several times, developed until the bands appear, and then added with the stop solution.

5. Experimental Results

Figure 7:
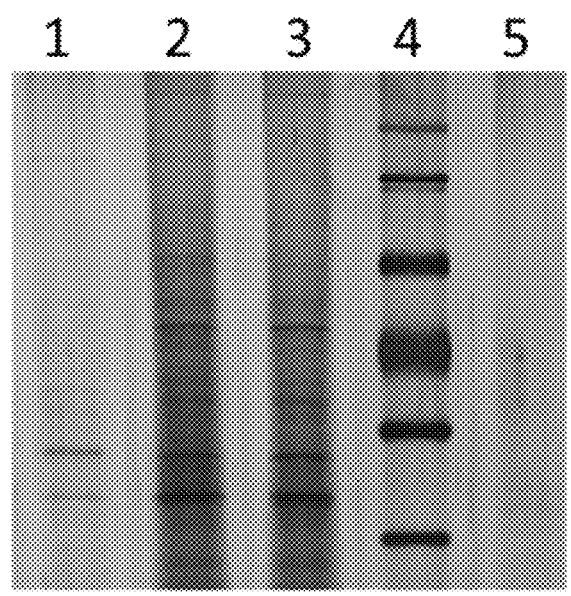
FIG. 7: lane 1: biotin, together with contrast compound 2, directly captures proteins from cell lysis buffer; lanes 2 and 3: whole-cell lysis buffer; lane 4: a scale for the molecular weight of proteins; lane 5: the proteins captured from the cell lysis buffer by Oligo(dT) magnetic beads, together with labeled compound 1, after the labeled compound 1 is transferred into cells to capture target proteins.

As shown in FIG. 7, by comparing the target capture directly performed in cell lysis buffer (lane 1) with the target capture in cells by penetrating through the cell membrane (lane 5), it is indicated that the method for capturing targets in cells contains less impure proteins and is easier in determining real targets. Furthermore, the target capture in cells, as based on cell phenotype response, has higher accuracy.

Embodiment 6

Identification and Sorting of Target Proteins, Captured by the Labeled Compound 1, by Proteomics 1. Identification of Targets 1.1 Analysis of differential proteins: the PAGE gel (FIG. 7) used for capturing target proteins and the blank control were provided to the BGI for protein analysis and comparison.

1.2 Sorting of potential target proteins: based on the comparison results in 2.1, cytoskeleton proteins and the like were removed from the differential proteins, and the potential target proteins were sorted by priority according to (relative) abundance (the results are as shown in FIG. 8).

Embodiment 7

Determination of Targets Captured by the Labeled Compound 1

1. Materials and Reagents

The human full-length PTP1B proteins were purchased from Sigma (Cat# SRP0215, Lot#3000920322); the substrate (4-nitrophenyl phosphate disodium salt (hexahydrate)) were purchased from Sigma (Cat#71768); and the buffer and the like used in the experiments were purchased from Sigma.

Figure 9:
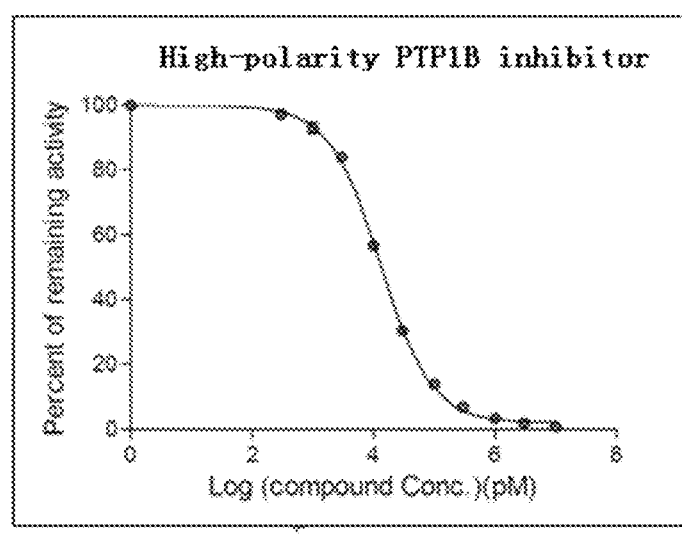
FIG. 9 shows measurement of IC50 value of unmodified compounds to PTP1B.

2. Determination of Target Proteins 2.1 Test on the inhibition of compounds to PTP1B: 10 μL of compounds in different concentrations was added to 90 μL of reaction system containing substrate and PTP1B, with a final concentration of 10 μM, 3 μM, 1 μM, 0.3 μM, 0.1 μM, 0.03 μM, 0.01 μM, 0.003 μM, 0.001 μM, 0.0003 μM and 0 μM, respectively; and the reaction lasted for 15 min at room temperature, and the absorption value was measured at 405 nm every 60 s. The relative percentage of the reaction rate at each concentration point was calculated, assuming the reaction rate without any compound (the amount of increase of the absorption value/the reaction time) as 100%. Curve fitting was performed, by GraphPad Prism drawing software, in a sigmoidal dose-response (variable slope) model, and the IC50 value of the compound to be tested was calculated (see FIG. 9).

2.2 By determining the identified targets by unmodified compounds for target identification one by one, it was found that the compounds inhibited only PTP1B. Therefore, it was determined that PTP1B was the target of the compounds in cells.

Embodiment 8

Synthesis and Transfer of the Labeled Compound 3

Synthesis Route of the Labeled Compound 3:

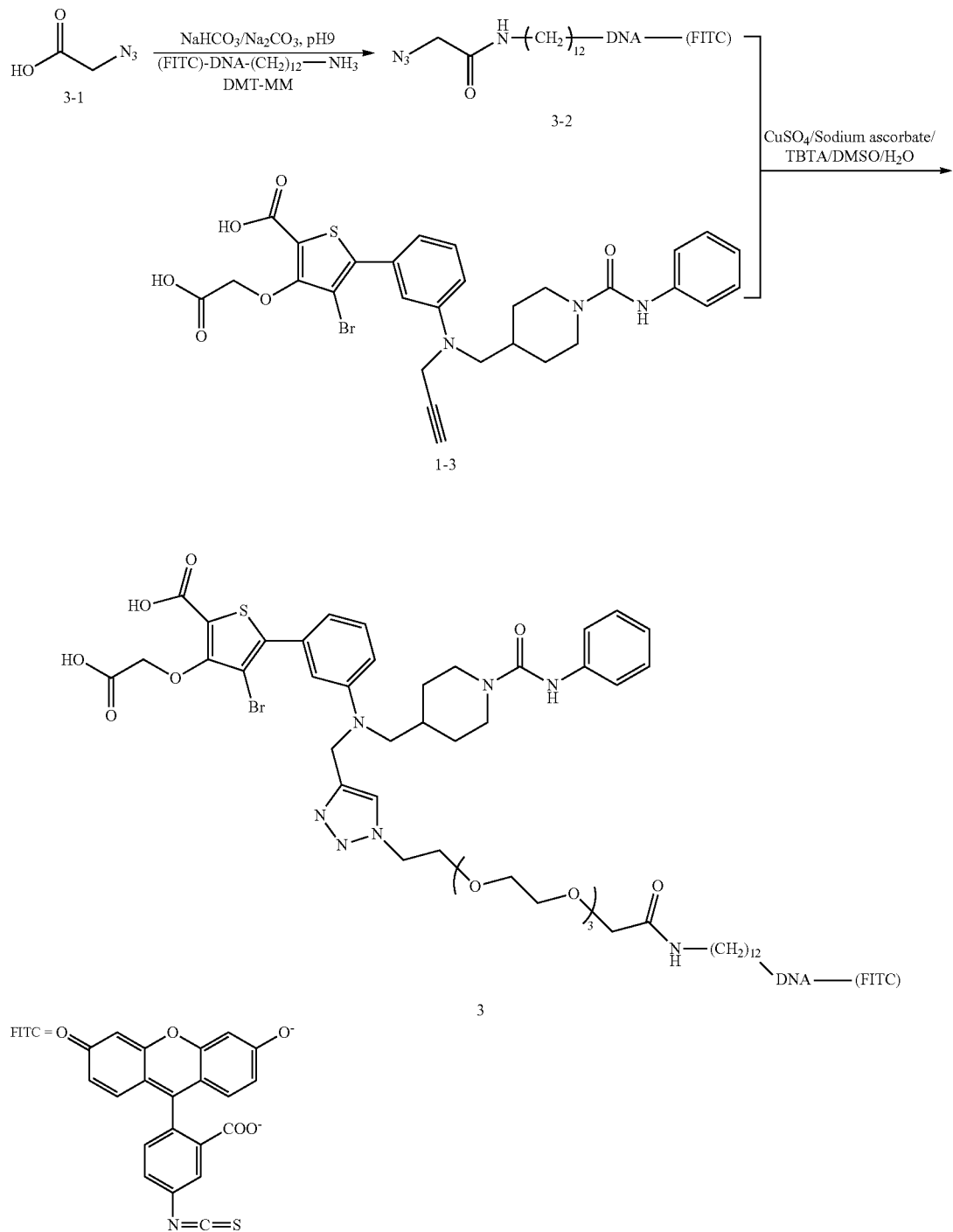

Compound 3-2:

A mixture of polyA (5'-(CH$_2$)$_{12}$-A$_{19}$-3'-FITC)(80 nmol) modified by 5'-amino and 3'-fluorescein, azidoacetic acid (compound 3-1) (1.6 μmol, 200 eq.), 4-(4,6-dimethoxytriazin-2-yl)-4-methyl morpholine hydrochloride (DMT-MM, 1.6 μmol, 200 eq.) in 80 μL of 0.5 M sodium carbonate/sodium bicarbonate buffer (pH 9), 160 μL of deionized water and 160 μL of dimethylsulfoxide was shaken overnight in a low speed at room temperature. Then, the reaction system was directly separated by reverse HPLC column chromatography and lyophilized to obtain compound (compound 3-2) (white solid). MS m/z (TOF): 6720

Labeled Compound 3:

60 μL of solution A (copper sulfate and tris[(1-benzyl-1H-1,2,3-triazol-4-yl)methyl]amine were dissolved at a mole ratio of 1:2 into a solution composed of water, dimethylsulfoxide and tert-butanol at a volume ratio of 4:3:1, with a concentration of 10 mM) was added to solution B (compound 3-2 (50 nmol) in 400 μL of aqueous solution and 4-bromo-3-oxoacetic acid-5-(3-(((1-phenyl carbamoylpiperidine)-4-methyl)-N-propargyl amine)phenyl)thiophene-2-formic acid (compound 1-3) (3 umol)) in 100 μL of DMSO solution, and vortex-centrifuged; and subsequently, 120 μL of newly-prepared sodium ascorbate (1200 nmol) in aqueous solution was added to the reaction system, and then shaken overnight in a low speed at room temperature. Then, the reaction solution was directly separated by reverse HPLC column chromatography and purified to obtain the labeled compound 3 (light yellow solid). MS m/z (TOF): 7345.

Figure 10:
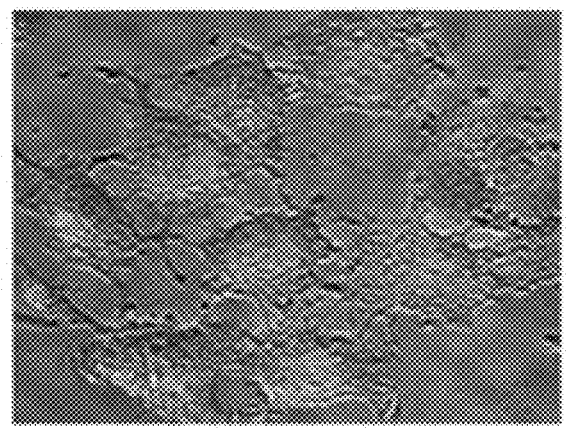
FIG. 10 shows positioning, by laser confocal microscopy, of the labeled compound 3 in cells (those in blue are cell nucleus, and those in green are FITC-tagged labeled compounds 3)

By a same transfer method as for the labeled compound 1 in Embodiment 3, the following results, by laser confocal microscopy, are as shown in FIG. 10: like the labeled compound 1, the labeled compound 3 may also be transferred into cells by X-tremesiRNA, with most of them into the cytoplasm and a few of them into the cell nucleus. The results indicate that a same compound, when linked to different DNA/RNA, may also be transferred into cells.

Embodiment 9

Synthesis and Transfer of the Labeled Compound 4

Synthesis Route of the Labeled Compound 4:

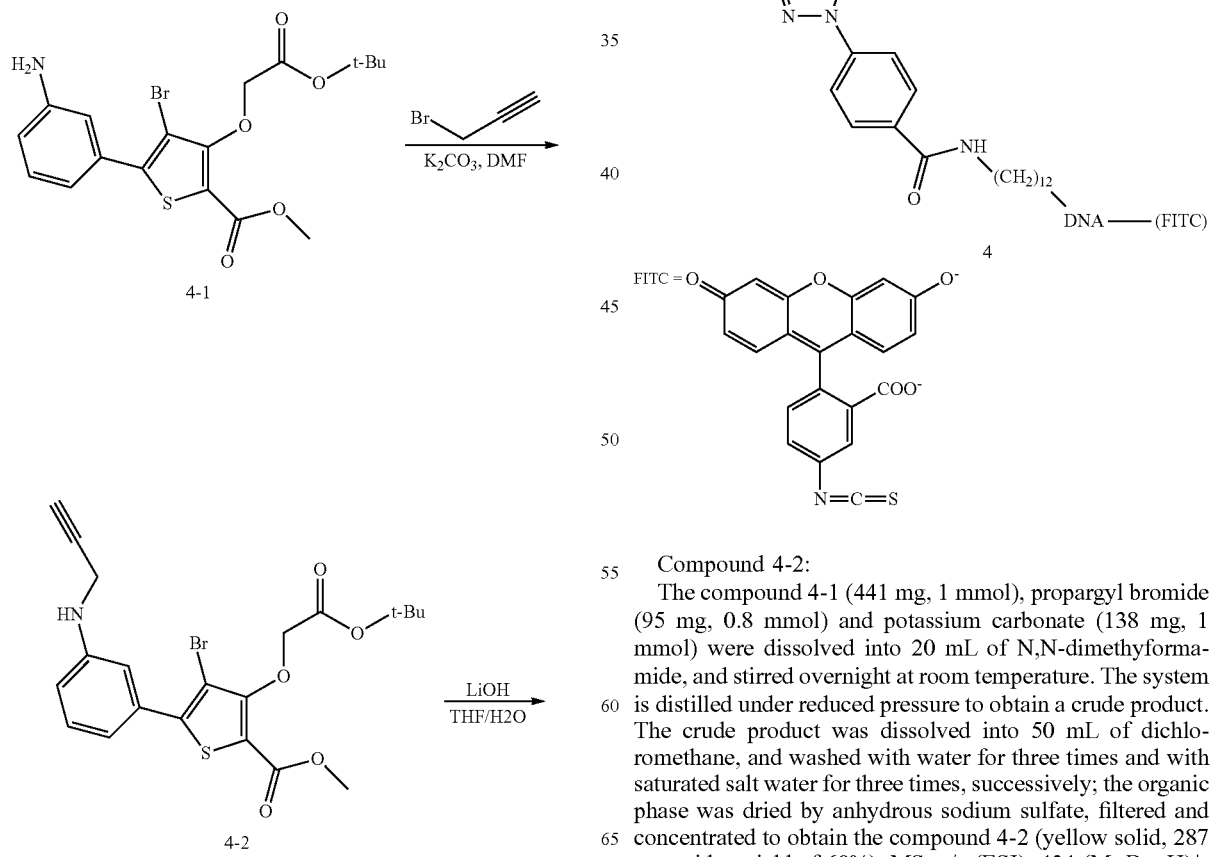

Compound 4-2:

The compound 4-1 (441 mg, 1 mmol), propargyl bromide (95 mg, 0.8 mmol) and potassium carbonate (138 mg, 1 mmol) were dissolved into 20 mL of N,N-dimethyformamide, and stirred overnight at room temperature. The system is distilled under reduced pressure to obtain a crude product. The crude product was dissolved into 50 mL of dichloromethane, and washed with water for three times and with saturated salt water for three times, successively; the organic phase was dried by anhydrous sodium sulfate, filtered and concentrated to obtain the compound 4-2 (yellow solid, 287 mg, with a yield of 60%). MS m/z (ESI): 424 (M-tBu+H)$^+$; 480 (M+H)$^+$.

Compound 4-3:

The compound 4-2 (87 mg, 0.6 mmol) and lithium hydroxide monohydrate (126 mg, 3 mmol) were dissolved into 5 mL of methanol and 5 mL of water, and reflux-stirred overnight. Ethanol was removed by distillation. The solution was diluted with 20 mL of water and acidified with 1N HCl until the pH became 2.0, and lyophilized to obtain a crude product; and the crude product was directly subject to reverse high-phase liquid-phase separation to obtain the compound 4-3 (yellow solid, 216 mg, with a yield of 80%). MS m/z (ESI): 410 (M+H)$^+$.

Labeled Compound 4:

60 μL solution A (copper sulfate and tris[(1-benzyl-1H-1,2,3-triazol-4-yl)methyl]amine were dissolved at a mole ratio of 1:2 into a solution composed of water, dimethylsulfoxide and tert-butanol at a volume ratio of 4:3:1, with a concentration of 10 mM) was added to solution B (the compound 4-4 (50 nmol) in 400 μL of aqueous solution and the compound 4-3 (3 umol) in 100 μL of DMSO solution), and vortex-centrifuged; and subsequently, 120 μL of newly-prepared sodium ascorbate (1200 nmol) in aqueous solution was added to the reaction system, and then shaken overnight in a low speed at room temperature. Then, the reaction solution was directly separated by reverse HPLC column chromatography and purified to obtain the labeled compound 4 (light yellow solid). MS m/z (TOF): 7191

Figure 11:
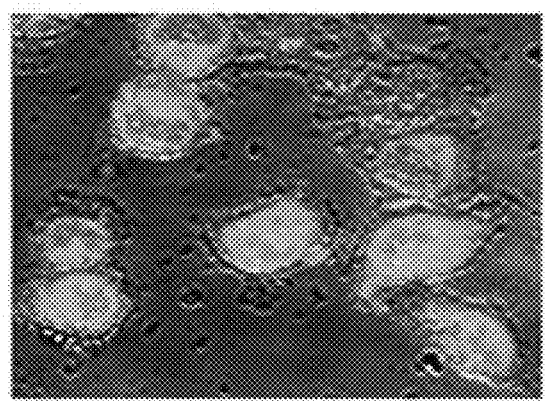
FIG. 11 shows positioning, by laser confocal microscopy, of the labeled compound 4 in cells (those in blue are cell nucleus, and those in green are FITC-tagged labeled compounds 4).

By a same transfer method as for the labeled compound 1 in Embodiment 3, the following results, by laser confocal microscopy, are as shown in FIG. 11: like the labeled compound 1, the labeled compound 4 may also be transferred into cells by X-tremesiRNA, with most of them into the cytoplasm and a few of them into the cell nucleus. The results indicate that different compound molecules may also be transferred into cells by the method of the present invention.

In conclusion, by the method of the present invention, drug targets in cells may be captured and verified effectively; and the method of the present invention provides more direct and more conclusive evidences for the acting mechanism of drugs.

The invention claimed is:

1. A method for capturing drug targets, comprising the following steps of:
   (1) Preparing a raw material comprising drug compounds and DNA, RNA or one part of other specific affinity materials;
   (2) Linking: covalently linking the drug compounds to the DNA, RNA or the one part of other specific affinity materials, to obtain labeled compounds;
   (3) Transferring: transferring the labeled compounds obtained in the step (2) into cells;
   (4) Capturing targets: disrupting the cells in the step (3), and then capturing the DNA or RNA in the step (1) by immobilized complementary DNA or RNA, or capturing the one part of specific affinity materials in the step (1) by the immobilized other part of the specific affinity materials, thus to enrich the targets;
   (5) Identifying targets; and
   (6) Determining targets.

2. The method according to claim 1, characterized in that, the target identification described in the step (5) is to dissociate the enriched targets from a stationary phase, deploy the enriched targets by a gel electrophoresis method, and compare differential proteins by proteomics thus to identify the potential targets; and
   the target determination described in the step (6) is to express the targets identified in the step (5) by priority, and compare by interaction of the compounds with those targets one by one to determine the targets for the compounds.

3. The method according to claim 1, characterized in that, in the step (1), the molecular weight of the compounds ranges from 100 Da to 4000 Da.

4. The method according to claim 1, characterized in that the DNA or RNA in the step (1) has a functional group for the covalent linkage to the compounds in the step (2).

5. The method according to claim 1, characterized in that, in the step (1), the length of the DNA or RNA is not less than five base pairs or bases.

SEQUENCE LISTING

```
<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: SEQ ID NO:1 is synthesized by Invitrogen
      Trading Shanghai Co., Ltd.

<400> SEQUENCE: 1
cagcagtttg gccagccca                                                19

<210> SEQ ID NO 2
<211> LENGTH: 19
<212> TYPE: DNA
<213> ORGANISM: Artificial Sequence
<220> FEATURE:
<223> OTHER INFORMATION: SEQ ID NO:2 is synthesized by Invitrogen
      Trading Shanghai Co., Ltd.

<400> SEQUENCE: 2
tgggctggcc aaactgctg                                                19
```

6. The method according to claim 1, characterized in that, in the step (1), the DNA or RNA is tagged with biotin or fluorescein or isotope or other tags for tracing.

7. The method according to claim 1, characterized in that the one part of other specific affinity materials in the step (1) is one part of any pair of specific affinity materials having covalent linkage to the compounds in the step (2).

\* \* \* \* \*